US011865231B2

(12) United States Patent
Eberle et al.

(10) Patent No.: US 11,865,231 B2
(45) Date of Patent: Jan. 9, 2024

(54) FRAGRANCING SYSTEM FOR A MOTOR VEHICLE (71) Applicant: Mahle International GmbH, Stuttgart (DE)

(72) Inventors: Daniel Eberle, Ludwigsburg (DE); Sham Kasar, Maharashtra (IN); Sven Petzner, Welzheim (DE); Oliver Schultze, Stuttgart (DE)

(73) Assignee: Mahle International GmbH

( * ) Notice: Subject to any disclaimer, the term of this patent is extended or adjusted under 35 U.S.C. 154(b) by 433 days.

(21) Appl. No.: 17/165,917

(22) Filed: Feb. 2, 2021

(65) Prior Publication Data
US 2021/0236681 A1  Aug. 5, 2021

(30) Foreign Application Priority Data

Feb. 3, 2020 (DE) .................... 102020201255.5

(51) Int. Cl.
*A61L 9/12* (2006.01)
*B60H 3/00* (2006.01)
(52) U.S. Cl.
CPC ............. *A61L 9/125* (2013.01); *B60H 3/0035* (2013.01); *A61L 2209/133* (2013.01); *A61L 2209/134* (2013.01); *B60H 2003/0064* (2013.01)

(58) Field of Classification Search
None
See application file for complete search history.

(56) References Cited

U.S. PATENT DOCUMENTS 6,713,024 B1  3/2004  Arnell et al.
10,661,636 B2  5/2020  Bauer et al.

FOREIGN PATENT DOCUMENTS

DE    102017201238 A1   7/2018
WO    WO-2004037304 A1   5/2004
WO    WO-2009003704 A2   1/2009

*Primary Examiner* — Jelitza M Perez
(74) *Attorney, Agent, or Firm* — Fishman Stewart PLLC (57) ABSTRACT A fragrancing system may include at least one cartridge for storing a fragrance and at least one closing mechanism. The cartridge may have a cartridge opening. The closing mechanism may include a flap, a shaft, a lever, and a pin. The flap may be displacable via the shaft to a closed position, in which the flap closes the cartridge opening, and an open position, in which the flap frees the cartridge opening. The fragrancing system may further include an actuating mechanism, which may have a disc rotatable via an actuator. A cam plate structure may project axially from the disc. The pin may be arranged on a radially outward facing outer side of the cam plate structure when the flap is in the closed position and may be engaged with a recess of the cam plate structure when the flap is in the open position.

20 Claims, 9 Drawing Sheets

FRAGRANCING SYSTEM FOR A MOTOR VEHICLE

CROSS-REFERENCE TO RELATED APPLICATIONS

This application claims priority to German Patent Application No. DE 10 2020 201 255.5, filed on Feb. 3, 2020, the contents of which is hereby incorporated by reference in its entirety.

TECHNICAL FIELD

The present invention relates to a fragrancing system for a motor vehicle, which has at least one cartridge for storing a fragrance, and a closing mechanism for opening and closing the cartridge. The invention relates furthermore to a module with such a cartridge and with the associated closing mechanism.

BACKGROUND

Fragrancing systems are used in particular in motor vehicles, in order to increase the comfort for the occupants of the motor vehicle, in particular in a passenger compartment of the motor vehicle. For this purpose, at least one fragrance is introduced through an air stream into the space which is to be fragranced. Such fragrancing systems usually have a cartridge in which the fragrance is stored. For the delivery of the fragrance, generally an air stream is directed through the cartridge, so that the air flow, on exiting from the cartridge and thus out of the fragrancing system, carries the fragrance with it. An increased comfort for the user is generally achieved in that such a fragrancing system has at least two cartridges, in which respectively associated fragrances are stored, so that the space which is to be fragranced can be fragranced with different fragrances. Such a fragrancing system is known for example from WO 2004/037304 A1.

For the optional fragrancing of the space which is to be fragranced with the fragrance, such fragrancing systems usually have a closing mechanism which in different positions releases or blocks a stream of air through the associated cartridge.

From WO 2009/003704 A2 a fragrancing system is known which has at least one cartridge for storing a fragrance, wherein a closing mechanism is associated with the respective cartridge. The respective closing mechanism has a flap which optionally releases or blocks a cartridge opening of the associated cartridge. Here, the respective flap is mounted in a non-rotatable manner on an associated shaft of the associated closing mechanism. The respective shaft is driven individually, in order to open or close the associated cartridge opening individually.

A disadvantage in fragrancing systems known from the prior art is the complex construction of the fragrancing system, in particular in the case of an increasing number of cartridges, which lead to correspondingly high production costs and/or to an increased vulnerability of the fragrancing system. In addition, for this reason the fragrancing systems are not operable, or only operable with difficulty, for a user. In particular, the exchange of cartridges proves to be difficult and uncomfortable for the user.

SUMMARY

The present invention is therefore concerned with the problem of indicating, for a fragrancing system of the type named in the introduction and for a module for such a fragrancing system, improved or at least different embodiments, which are distinguished in particular by a simplified production and/or an increased robustness and/or an improved user-friendliness.

This problem is solved according to the invention by the subject matter of the independent claim(s). Advantageous embodiments are the subject matter of the dependent claim(s).

The present invention is based on the general idea, in a fragrancing system, of closing and opening a cartridge, serving for storing a fragrance, with a flap which is actuated by means of a cam plate. The flap can thus be displaced and the corresponding mechanism can be configured in a space-saving and mechanically robust manner. Moreover, in this way it is possible to close and open several cartridges in the fragrancing system in the same manner and with the same cam plate, so that the space-saving construction and the robustness of the fragrancing system also continue to exist in the case of several cartridges. In this way, the fragrancing system can be equipped further in a simplified manner and optionally exchangeably with at least one cartridge, preferably several cartridges, so that the handling of the fragrancing system and thus the user-friendliness is improved.

In accordance with the idea of the invention, the fragrancing system has at least one cartridge for storing a fragrance, and a closing mechanism associated with the respective cartridge. The respective cartridge has an opening, also designated below as cartridge opening, through which an air stream can flow in order, on exiting from the cartridge, to carry the fragrance into a space and to thus fragrance this space. The respective closing mechanism has a flap and a shaft with which the flap is connected in a non-rotatable manner. The shaft extends here along an axial direction. The shaft is rotatable here about a pivot axis running parallel to the axial direction. Accordingly, the flap, which is connected with the shaft in a non-rotatable manner, is displaced through the rotation of the shaft about the pivot axis. Here, the flap is displaceable between a closed position, in which the flap closes the associated cartridge opening, and an open position, in which the flap releases the associated cartridge opening. The respective closing mechanism has, furthermore, a lever running transversely to the shaft, in particular projecting from the shaft, and connected mechanically with the shaft, and an axially-running pin, in particular projecting axially from the lever, and connected with the lever. The fragrancing system has, furthermore, an actuating mechanism with a disc which is rotatable about a rotation axis running in axial direction. A cam plate structure, running in circumferential direction, projects axially from the disc. Here, the respective pin in the closed position of the associated flap is arranged on the radially outer side of the cam plate structure, facing away from the rotation axis. The respective closing mechanism is configured in such a way that it acts upon the associated flap elastically in the direction of the closed position, and upon the associated pin elastically in the direction of the radial outer side of the cam plate structure. The cam plate structure has in the radial outer side for the at least one pin at least one recess, in which the pin in the open position of the associated flap engages through the elastic impingement. The cam plate structure therefore has in the radial outer side at least one recess, wherein at least one of the at least one pins in the open position of the associated flap engages into the recess through the elastic impingement. The pin is thus acted upon into the recess, whereby the pin rotates the shaft via the lever and thus displaces the flap into the open position. The fragrancing system has, furthermore, an actuator which, in operation, rotates the disc about the rotation axis.

The present direction indications refer in particular to the axial direction which runs parallel to the at least one pivot axis and the rotation axis, preferably coaxially to the rotation axis. Accordingly, the circumferential direction runs about this axial axis and the radial direction runs transversely to the axial direction.

Advantageously, the rotation axis and the at least one pivot axis run in a parallel manner and are spaced apart with respect to one another. In particular, the at least one pivot axis is spaced apart radially with respect to the rotation axis.

The actuator can basically be configured in any desired manner, in so far as it rotates the disc about the rotation axis during operation. In particular, the actuator is an electric motor.

Embodiments are preferred in which the fragrancing system has at least two closing mechanisms with respectively associated cartridges. The fragrancing system can thus be used in a more varied and more individual way. In particular, through the storing of different fragrances in the various cartridges, a more individual fragrancing can take place of the space which is to be fragranced.

It is preferred here if the cam plate structure has a shared recess for at least two of the pins, advantageously for all the pins. This means that the cam plate structure has a shared recess in the radial outer side for at least two of the pins, advantageously for all the pins. In particular, the cam plate structure can have only one single such recess for all the pins. The fragrancing system can thus be produced simply and in a space-saving manner. In addition, the robustness of the actuating mechanism and thus of the fragrancing system is thus increased. Moreover, in this way the cartridges can be opened individually and successively, so that a mixing of the fragrances and/or an unintentional fragrancing are prevented or at least reduced.

Embodiments prove to be advantageous, in which at least one of the at least one pins, in particular the respective pin, slides outside the open position and during the rotation of the disc about the rotation axis on the radial outer side of the cam plate structure. In this way, the respective closing mechanism is guided via the pin on the radial outer side of the cam plate structure. This leads to a simplified and defined displacing of the respective flap between the open position and the closed position.

Embodiments are preferred in which the cam plate structure is configured, in particular formed, in such a way that the respective pin on the rotation of the disc about the rotation axis in a first direction, for example clockwise with respect to the rotation axis, is acted upon into the at least one recess of the cam plate structure, whereas the pin on a rotation of the disc about the rotation axis in a second direction opposed to the first direction, for example anticlockwise, slides over the at least one recess. In this way it is possible, by a rotation of the disc in the second direction, to select the closing mechanism which is to be actuated, i.e. at which the flap is to be displaced from the closed position into the open position, and to displace the flap in a targeted manner into the open position by a rotation in the first direction via the associated pin without the at least one flap being displaced into the open position on rotating of the disc about the second direction. This leads to a simplified implementation of the fragrancing system and an unequivocal and reliable opening and closing of the respective flap, i.e. a displacing of the respective flap between the open position and the closed position.

For this purpose, the cam plate structure can basically be configured in any desired manner.

In particular, the recess can be formed in such a way that on the rotation of the disc in the first direction, the respective pin is acted upon into the recess, and on the rotation of the disc in the second direction, the respective pin slides over the recess.

For this purpose, it is conceivable to form the recess in such a way that it has a curvature following the second direction, therefore in particular anticlockwise. This means in particular that the recess has a radially outer external opening, from which the recess runs in a curved manner, following the second direction. The external opening is therefore arranged in particular in circumferential direction along the clockwise direction externally and in anticlockwise direction internally, when the second direction corresponds to the clockwise direction.

Embodiments are preferred in which the fragrancing system has at least two cartridges with a respectively associated closing mechanism, which are spaced apart with respect to one another in circumferential direction. In particular, the cartridges together with associated closing mechanism are spaced apart with respect to one another along the cam plate structure. Thus the cartridges and the closing mechanisms, in a top view in axial direction are arranged in particular in a circular or circular segment-shaped manner. The fragrancing system can thus be constructed and produced in a space-saving and simple manner. Moreover, in this way that closing mechanisms can be produced and actuated in a simple, space-saving and robust manner.

The respective cartridge opening can be arranged in any desired manner relative to the associated cartridge.

Preferably, at least one of the at least one cartridge openings, advantageously the respective cartridge opening, is arranged radially externally to the associated cartridge. In particular, at least one of the at least one cartridge openings runs tangentially to the circumferential direction. In particular, the flap thus also in the closed position runs tangentially to the circumferential direction. The respective cartridge can thus be closed easily and reliably. It is conceivable here that the respective cartridge opening is arranged on the side of the associated cartridge facing away radially from the rotation axis.

Basically, at least one of the at least one cartridges can be securely incorporated and integrated into the fragrancing system.

It is preferred if at least one of the at least one cartridges, advantageously the respective cartridge, is arranged exchangeably in the fragrancing system. It is particularly preferred here if the respective cartridge is able to be inserted along the axial direction into the fragrancing system. The respective cartridge can thus be mounted easily and in a user-friendly manner into the fragrancing system and/or exchanged.

Basically here at least two of the at least two cartridges can be configured differently.

Embodiments are preferred, in which at least two of the at least two cartridges are configured identically. The cartridges therefore concern in particular identical components. This does not necessarily apply to the fragrance which is stored in the respective cartridge. This means that the cartridges, despite identical construction, can store different fragrances.

It is advantageous if the lever and the pin of at least one of the at least one closing mechanisms, preferably of the respective closing mechanism, are produced jointly in one piece. The lever and the pin can therefore be produced in particular jointly for example from plastic. This leads to a favourably priced and simple production of the fragrancing system.

The elastic action upon the pin and upon the flap by the closing mechanism can basically be configured in any desired manner.

In particular, one of the at least one closing mechanisms can have a spring which acts upon the flap in the direction of the closed position, and another spring, which acts upon the pin in the direction of the outer side of the cam plate structure.

It is preferred if at least one of the at least one closing mechanisms has a rotary spring which is wound around the pivot axis of the associated shaft, in particular around the shaft, wherein the rotary spring acts with a first projecting leg upon the flap in the direction of the closed position, and with a second projecting leg acts upon the pin in the direction of the outer side of the cam plate structure. The action upon the flap and upon the pin can thus be implemented effectively and at a favourable cost and in a robust manner. The legs can project here from the rotary spring from axially opposite ends of the rotary spring.

When the fragrancing system has two closing mechanisms, the closing mechanisms can basically be configured differently.

It is preferred if at least two of the at least two closing mechanisms, preferably all closing mechanisms, are configured in an identical manner. The fragrancing system can thus be produced simply and at a favourable cost.

When both the cartridges and also the closing mechanisms are configured respectively as identical parts, the fragrancing system can, in addition, be used universally. In particular, the cartridges can thus be respectively personalized as desired and according to individual wishes and inserted in a changeable manner into the fragrancing system and exchanged.

Advantageous embodiments provide a chamber of the fragrancing system, in which the at least one cartridge is arranged. Here, a flow path leads through the chamber, in order to carry out of the chamber fragrance from at least one of the at least one cartridges for the purpose of fragrancing a space. It is thus possible in particular to respectively fragrance the space individually with fragrance via the same flow path by the individual opening and closing of the flaps.

It is preferred if the flow path runs through an inlet opening which is spaced apart with respect to the at least one cartridge, and through an outlet opening which is spaced apart with respect to the at least one cartridge. This means that air arrives into the chamber and flows out from the chamber through openings which are spaced apart with respect to the cartridges and consequently also with respect to the cartridge openings. In this way, it is in particular prevented that a fragrance arrives unintentionally into the corresponding air stream or the corresponding risk is at least reduced. In addition, it is possible in this way, by the closing of all of the at least one flaps, to flush the chamber so that in a subsequent fragrancing no undesired mixing of fragrances occurs.

Of course, it is conceivable that at least two inlet openings and/or at least two outlet openings are provided, through which respectively the flow path leads, wherein the respective inlet opening and outlet opening is preferably spaced apart with respect to the respective cartridge, in particular to the respective cartridge opening.

It is advantageous if a conveying device, in particular a fan, arranged at the downstream side of the at least one outlet opening, draws air out of the at least one outlet opening. It is thus possible in particular to fragrance in a targeted and efficient manner the space which is to be fragranced, and/or to prevent a mixing of different fragrances and/or to fragrance the chamber in a simplified manner.

Embodiments are considered to be advantageous, in which the fragrancing system has a cylindrical casing which surrounds the at least one cartridge and the at least one closing mechanism in circumferential direction. In particular, the cylindrical casing at least partially forms or delimits the chamber. This enables a compact design of the fragrancing system and a simplified and/or variable use, in particular installation, of the fragrancing system in the associated application.

The rotation of the disc about the rotation axis by means of the actuator can basically take place in any desired manner.

Embodiments are preferred in which an output shaft projects axially from the disc on the side facing away axially from the cam plate structure, which output shaft expediently runs coaxially to the rotation axis and via which the actuator rotates the disc about the rotation axis. In particular, the output shaft can be produced in one piece and jointly with the disc and the cam plate structure. The fragrancing system can thus be produced in a space-saving and robust manner. It is conceivable here to provide the output shaft with an output gearwheel or to connect it therewith, which output gearwheel is driven by a drive gearwheel of the actuator, which is connected with a drive shaft of the actuator.

Advantageous embodiments have in at least one of the at least one cartridges a seal surrounding the cartridge opening, which is softer than the associated flap and on which the flap rests in a sealing manner in the closed position. The flap opening in the closed position of the associated flap can thus be closed in a sealing manner effectively and in a simplified way. In addition, in this way the noise generation on displacing the flap is reduced, so that the use of the fragrancing system is more pleasant for a user.

The fragrancing system can basically be used in any desired application. In particular, the fragrancing system is used in a motor vehicle, in order to fragrance an interior of the motor vehicle in particular a passenger compartment of the motor vehicle, with fragrance. For this purpose, an air stream is guided along the flow path through the fragrancing system. The fragrancing system here can be in particular a component part of a ventilation and/or air-conditioning system, in particular of the motor vehicle.

Preferably, at least one of the cartridges together with the associated closing mechanism is present as a module which can be exchangeably inserted into the fragrancing system and removed from the fragrancing system. The fragrancing system can thus be equipped individually with modules. Consequently, it is possible to equip the fragrancing system individually with modules which store different fragrances in the associated cartridge, and/or to exchange the modules in a simplified manner. The inserting of the modules into the fragrancing system takes place here preferably by a pushing-in or plugging-in along the axial direction.

It shall be understood here that in addition to the fragrancing system, the module as such also belongs to the scope of this invention.

Further important features and advantages of the invention will emerge from the subclaims, from the drawings and from the associated figure description with the aid of the drawings.

It shall be understood that the features mentioned above and to be further explained below are able to be used not only in the respectively indicated combination, but also in other combinations or in isolation, without departing from the scope of the present invention.

Preferred example embodiments of the invention are illustrated in the drawings and are explained more closely in the following description, wherein the same reference numbers refer to identical or similar or functionally identical components.

BRIEF DESCRIPTION OF THE DRAWINGS

There are shown, respectively schematically.

DETAILED DESCRIPTION

Figure 1:
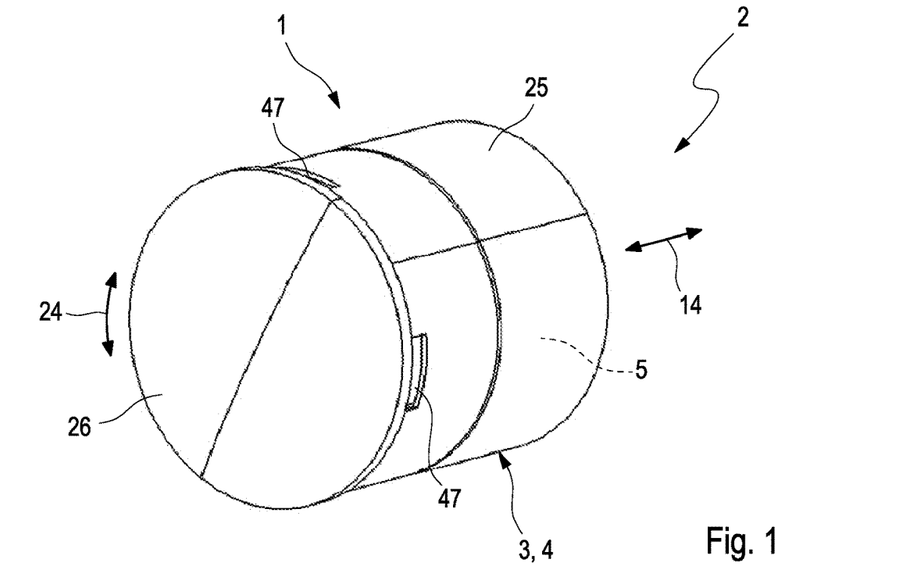
FIG. 1 shows an isometric view of a fragrancing system.

A fragrancing system 1, as is shown for example in FIGS. 1 to 12 and 14 and 15, is used in particular in a motor vehicle 2, which is otherwise not shown, in order to fragrance a vehicle interior, which is not shown. The shown fragrancing system 1 has a casing 3, in particular a housing 4, which is configured cylindrically and surrounds and delimits a chamber 5. FIG. 1 shows here an isometric external view of the fragrancing system 1, in which substantially only the casing 3 is to be seen or respectively the chamber 5 is not visible. By comparison, FIGS. 2 to 12 and 14 and 15 show respectively views of the fragrancing system 1 in which the chamber 5 is visible.

For fragrancing, the fragrancing system 1 has at least one cartridge 6, in which a fragrance 7, not shown, is stored. The respective cartridge 6 has an opening 7, also designated below as cartridge opening 7. As indicated in particular in FIG. 14 by arrows, a flow path 8, in particular of air, leading through the chamber 5, can lead through the cartridge opening 7, in order to receive fragrance and to introduce it into the space which is to be fragranced. For the respective cartridge 6 an associated closing mechanism 9 is provided, by which the cartridge opening 7 of the associated cartridge 6 can be released and closed. For this purpose, the respective closing mechanism 9 has a flap 10, a shaft 11, a lever 12 and a pin 13. The shaft 11 runs along an axial direction 14, i.e. in particular parallel to the axial direction 14, and is connected non-rotatably with the flap 10. The lever 12 is connected non-rotatably with the shaft 11 and runs transversely to the shaft 10, in particular projects transversely from the shaft 11. The pin 13 is connected with the lever 12 in an offset manner to the shaft 11 and extends axially. By a rotation of the respective shaft 11 about a pivot axis 15 associated with the shaft 11, which runs axially, in particular coaxially to the shaft 11, the associated flap 10, connected non-rotatably with the shaft 11, is displaceable between a closed position 16 and an open position 17. In the closed position 16, the flap 10 closes the cartridge opening 7 of the associated cartridge 6. By comparison, in the open position 17 the flap 10 frees the cartridge opening 7 of the associated cartridge 6.

Figure 2:
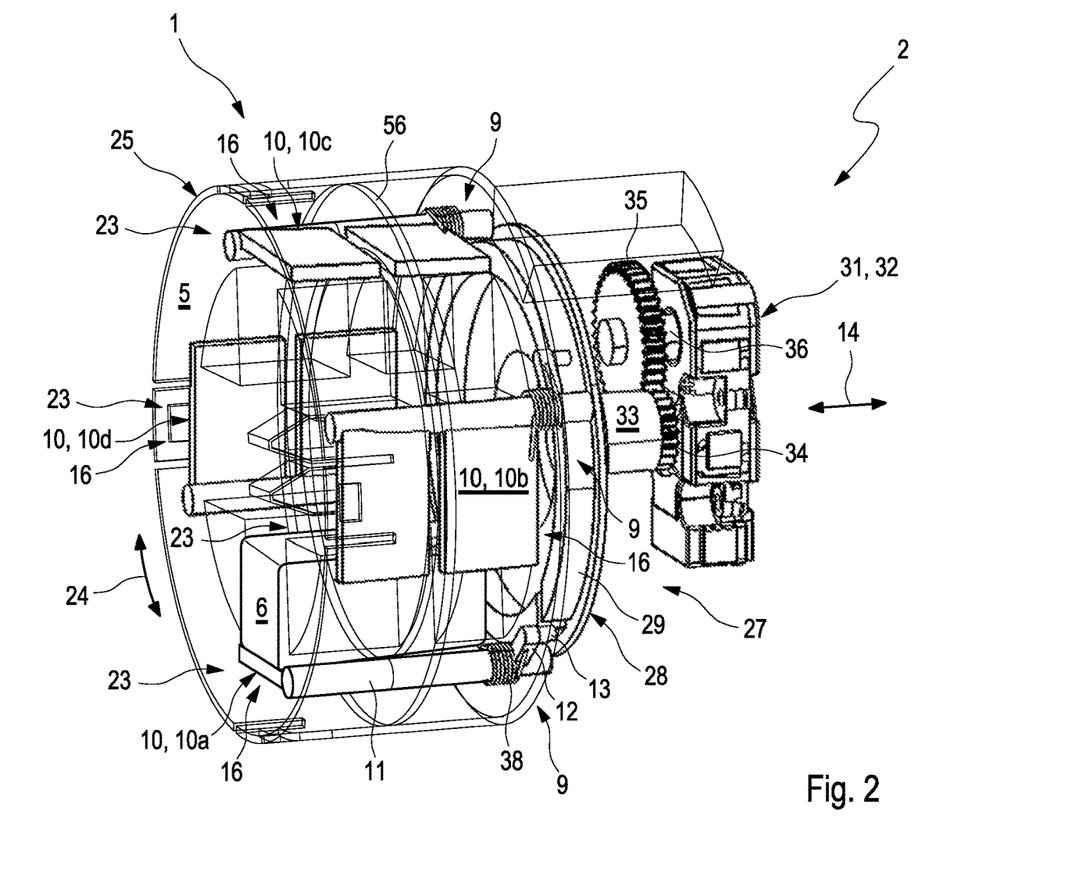
FIG. 2 shows an isometric and partially transparent view of the fragrancing system.

In the example embodiments which are shown, the fragrancing system 1 has purely by way of example four cartridges 6 and thus four closing mechanisms 9 and consequently four flaps 10, namely a first flap 10a, a second flap 10b, a third flap 10c and a fourth flap 10d. Here, the cartridges 6 and the closing mechanisms 9 are respectively preferably constructed identically. For a better understanding, only one of the cartridges 6 are shown in FIGS. 2 to 4 and 7 to 12. In the example embodiments which are shown, the respective cartridge 6 is configured, purely by way of example, in a substantially cuboid shape. The cartridge opening 7 of the respective cartridge 6 is preferably arranged and formed radially on the outer side of the cartridge 6. In the example embodiments which are shown, the respective cartridge opening 7 is divided axially into two by a centre web of the cartridge 6, therefore has a first opening portion 19 and a second opening portion 20 which is spaced apart axially with respect to the first opening portion 19 by the centre web 18. The respectively associated flap 10 is divided in two in an analogous manner hereto. This means that the respective flap 10 for the first opening portion 19 has an associated first flap portion 21 and a second flap portion 22 spaced apart axially with respect to the first flap portion 21 and associated with the second opening portion 20. Here, the respective cartridge 6 and the associated closing mechanism 9 can form a module 23, which is received in an exchangeable manner into the fragrancing system 1. For this purpose, the respective module 23 is preferably inserted axially into the fragrancing system 1 and removed from the fragrancing system 1. In particular for this purpose the casing 3 has a hollow-cylindrical pot-like casing portion 25, surrounding the chamber 5 in a circumferential direction 24, and a cover 26, axially closing the casing portion 25 and only illustrated in FIG. 1, which cover is detachable from the casing portion 25 for the exchanging of the modules 23. Here in FIG. 2 only the casing portion 25 of the casing 3 is illustrated, wherein the casing portion 25 is shown in a transparent manner. In FIG. 4, however, the illustration from FIG. 2 is shown entirely without casing 3.

The cartridges 6 and the closing mechanisms 9 are arranged respectively spaced apart with respect to one another in circumferential direction 24, at a section shown for example in FIGS. 7 to 12 transversely to the axial direction 14, therefore substantially in a circular shape.

For displacing the respective flap 10, the fragrancing system 1 has an actuating mechanism 27. The actuating mechanism 27 has a disc 28, which is arranged on the side of the cartridges 6 facing away axially from the cover 26 and extends transversely to the axial direction 14. A cam plate structure 29 projects from the disc 28 on the side facing the cartridges 6 axially, which cam plate structure extends in circumferential direction 24. The disc 28 is rotatable about a rotation axis 30 running in axial direction 14, in particular coaxially to the axial direction 14, which rotation axis is spaced apart radially with respect to the pivot axes 15 and in the shown example embodiments runs parallel to the pivot axes 15. The disc 28 and thus the cam plate structure 29 therefore, in operation, rotate respectively about the rotation axis 30. For rotating the disc 28 and thus the actuating mechanism 27, the fragrancing system 1 has an actuator 31 which can be, for example, an electric motor 32. For this purpose, on the side facing axially away from the cam plate structure 29, the disc 28 can have an output shaft 33 projecting coaxially with respect to the axial direction 14 or respectively rotation direction 30, which output shaft cooperates via an output gearwheel 34 with a drive gearwheel 35, which is mounted non-rotatably on a drive shaft 36 of the actuator 31, wherein drive shaft 36 and output shaft 33 are spaced apart radially with respect to one another.

In the closed position 16 of the associated closing mechanism 9, the respective pin 13 is arranged on a radial outer side 37 of the cam plate structure 29. In particular, the respective pin 13, in the closed position 16, slides on a rotation of the disc 28 about the rotation axis 30 along the outer side 37. The closing mechanism 9 is configured here in such a way that it acts upon the associated flap 10 elastically in the direction of the closed position 16 and upon the associated pin 13 elastically in the direction of the radial outer side 37. For this purpose, in the shown example embodiments, the respective closing mechanism 9 has a rotary spring 38, which is wound around the associated pivot axis 15 and has a first projecting leg 39, which acts upon the associated flap 10 in the direction of the closed position 16. In addition, the rotary spring 28 has a second leg 40, spaced apart axially with respect to the first leg 39, which second leg acts upon the associated pin 13, in particular via the lever 12, in the direction of the radial outer side 37 of the cam plate structure 29. When the pin 13 lies against the outer side 37, then this prevents the flap 10 from being displaced into the open position 17. The associated cartridge opening 7 is thus reliably closed. For displacing the respective flap 10 into the open position 17, the cam plate structure 29 has on the outer side 37 at least one recess 41. In the shown example embodiments, the cam plate structure 29 has only one such recess 41. This means that for displacing the respective flap 10 into the open position 17, the same recess 41 comes into use. For displacing the respective flap 10 into the open position 17, the cam plate structure 29 is moved by a rotation of the disc 28 about the rotation axis 30 to the pin 13 associated with the flap 10 in such a way that the pin 13 is acted upon in the direction of the outer side 37 and into the recess 41. Consequently, the associated shaft 11 rotates about the pivot axis 15 via the lever 12, and the associated flap 10 is displaced into the open position 17.

Figure 7:
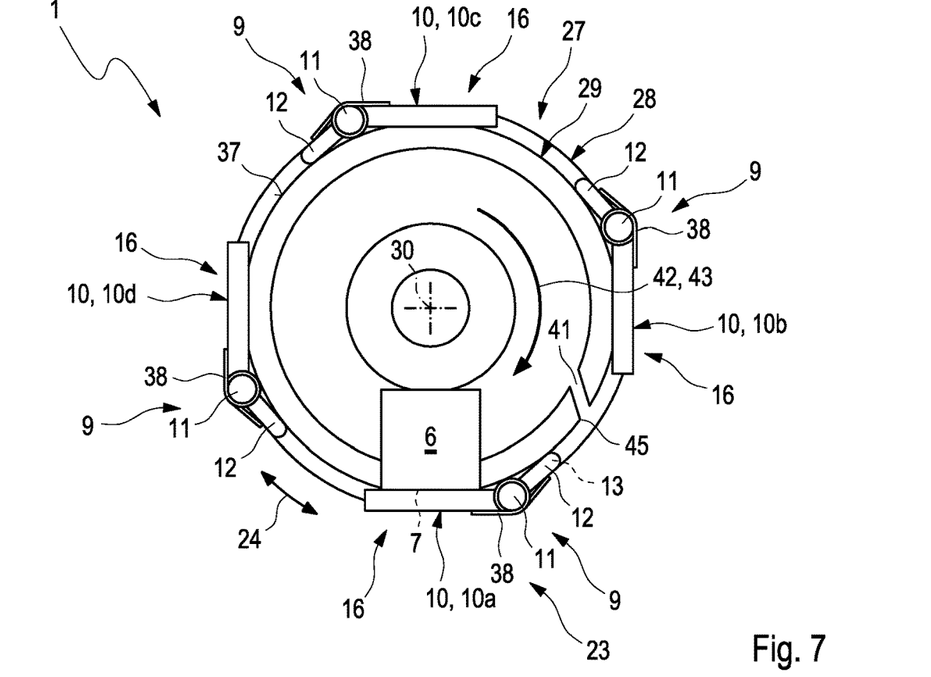
FIGS. 7 through 9 show a section through the fragrancing system at different positions on a rotation in a first direction.
Figure 8:
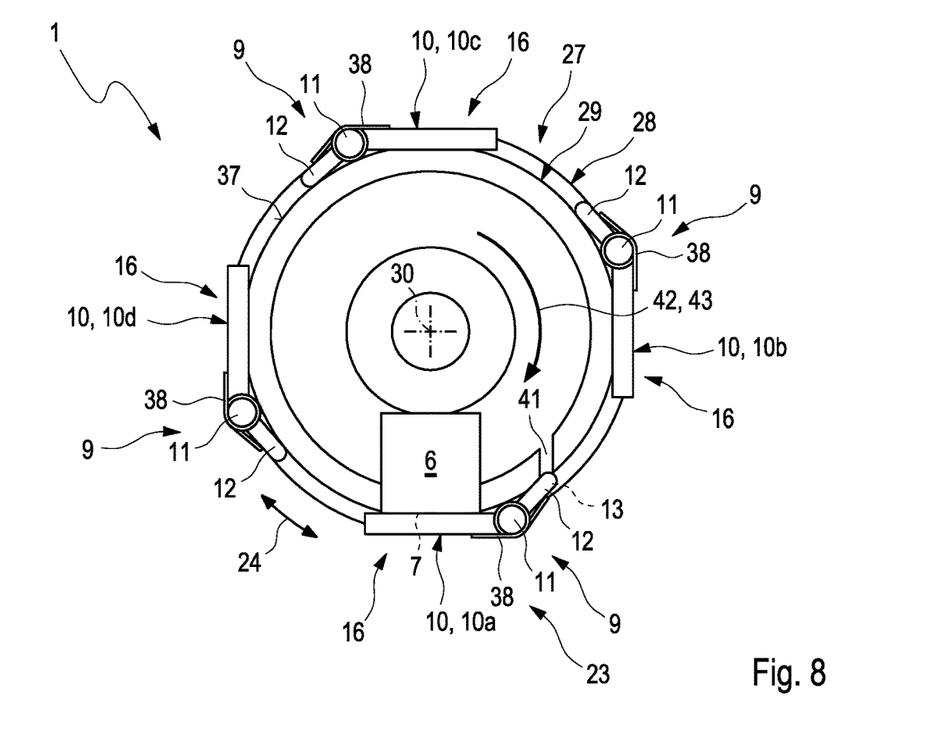
Figure 9:
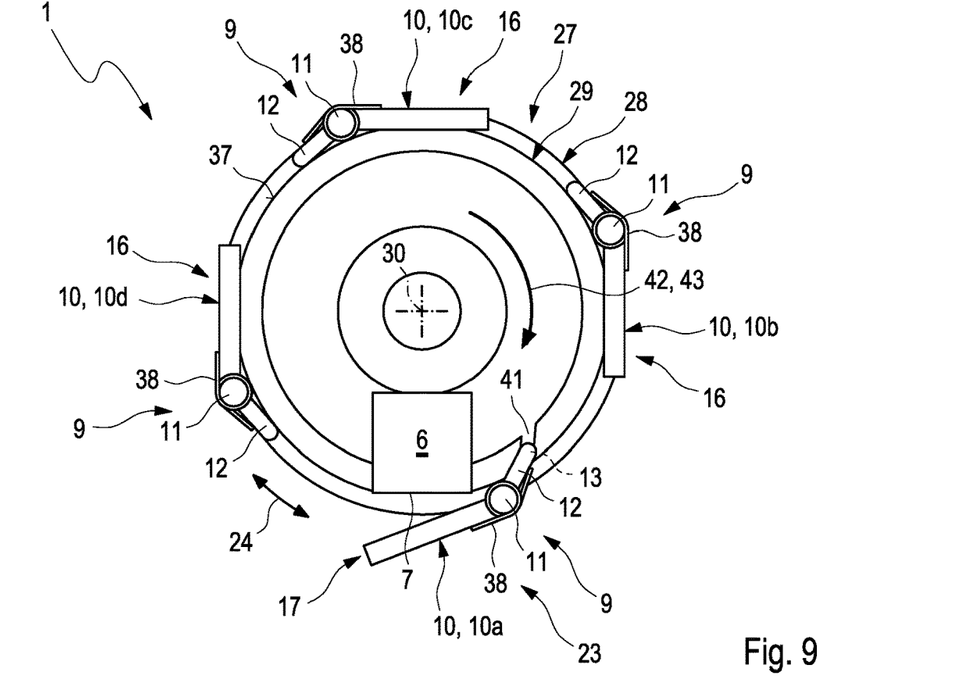
Figure 10:
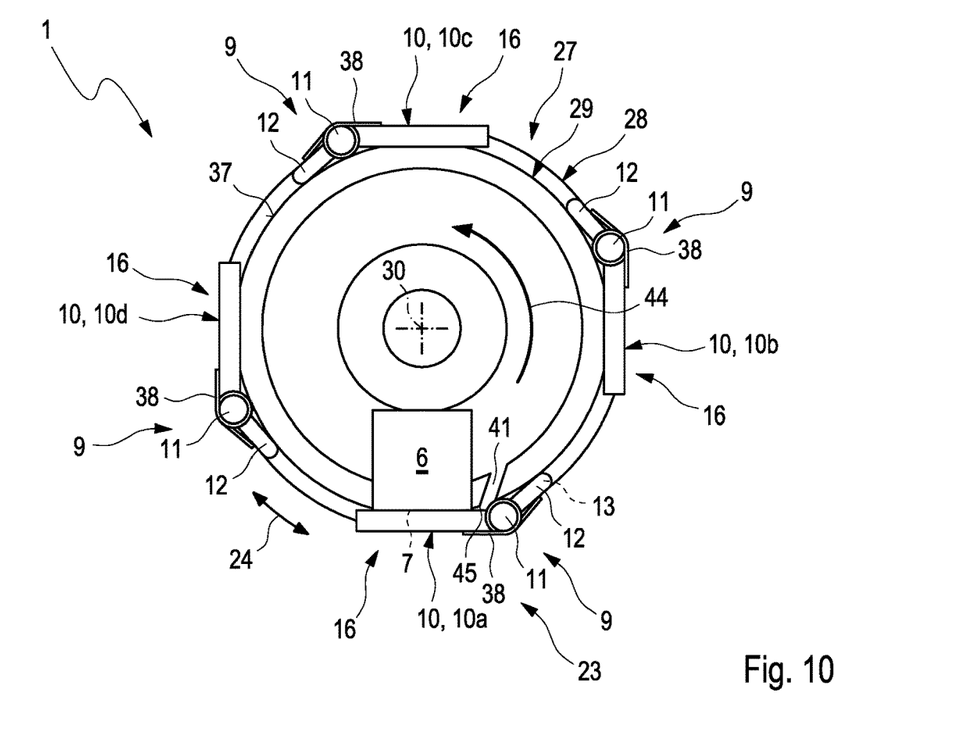
FIGS. 10 through 12 show a section through the fragrancing system at different positions on a rotation in a second direction.

As can be seen in particular from FIGS. 7 to 12, the recess 41 is configured, in particular formed, here in such a way that on a rotation of the disc 28 and thus of the cam plate structure 29 about the rotation axis 30 in a first direction 42 shown in FIGS. 7 to 9, which in the shown example embodiments corresponds to the clockwise direction 43 with respect to the rotation axis 30, the respective pin 13 on a corresponding relative positioning to the recess 41 is acted upon into the recess 41. By comparison, on a rotation of the disc 28 and thus of the cam plate structure 29 shown in FIGS. 10 to 12 about the rotation axis 20 in a second direction 44 opposed to the first direction 42, which in the shown example embodiments is therefore contrary to the clockwise direction 43, the respective pin 12 slides over the recess 41. For this purpose, in the example embodiments, the recess 41 in the first direction 42 is formed following from radially inside to radially outside. This means in particular that the recess 41 has a radially exterior outer opening 45, which is arranged in circumferential direction 24 and on the outer side following the first direction 42. In other words, the recess 41 extends starting from the outer opening 45 radially inwards and contrary to the first direction 42 and thus along the second direction 44. FIGS. 7 to 9 show different states here on a rotation of the disc 28 in first direction 42.

Figure 11:
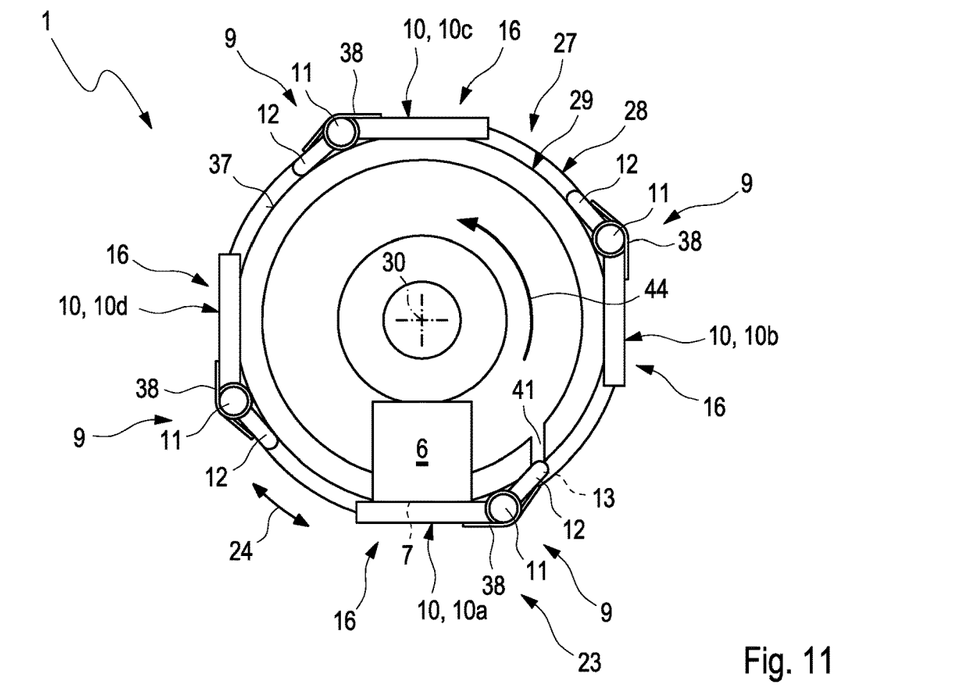
Figure 12:
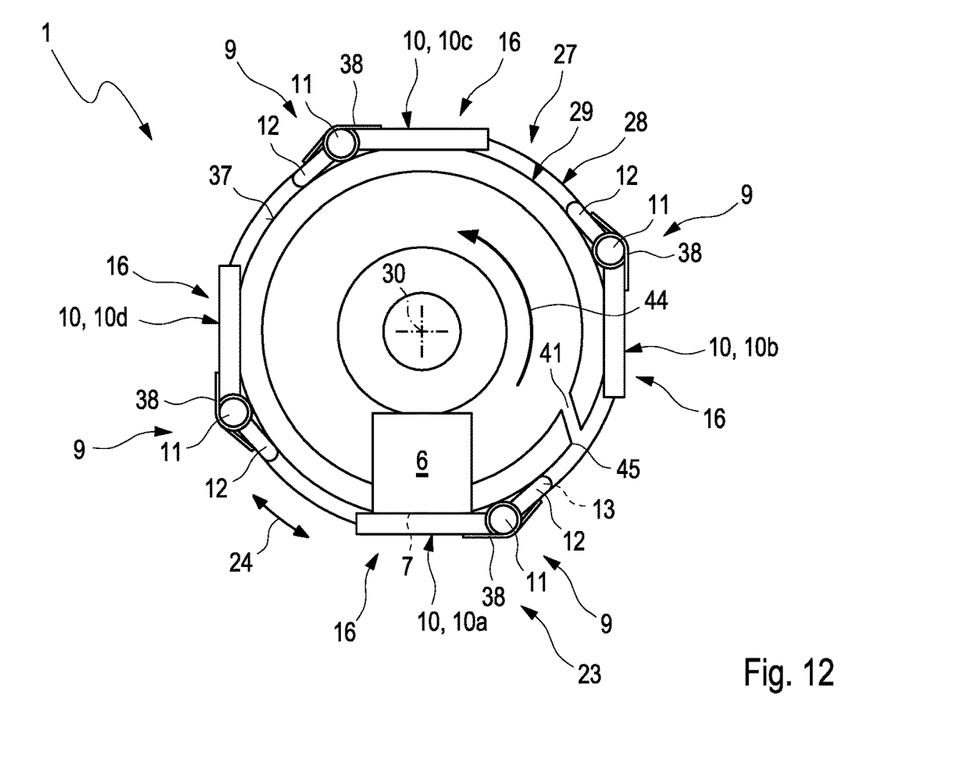

In the relative positioning of the recess 41 with respect to the pins 13, shown in FIG. 7, all the flaps 10 are situated in the closed position 16. When the disc 28 is rotated in first rotation direction 42, then in the relative positioning shown in FIG. 8 the pin 13 of the lower closing mechanism 9 shown in FIGS. 7 to 9 and thus the pin 13 associated with the first flap 10s comes into overlap with the outer opening 45. On a further rotation in first direction 42, the pin 13 is acted upon into the recess 41 and the first flap 10a is thus displaced into the open position 17, as is to be seen in FIG. 9. By comparison, on the rotation, shown in FIGS. 10 to 12, into second direction 44, an action upon the respective pin 13 into the recess 41 is prevented. Here, in particular FIGS. 11 and 12 show on a rotation of the disc 28 in second direction 44 the sliding along or respectively sliding past of the pin 13, again of the lower closing mechanism 9 in the illustration, and thus of the first flap 10a, over the recess 41, so that the associated first flap 10a remains continuously in the closed position 16.

Figure 13:
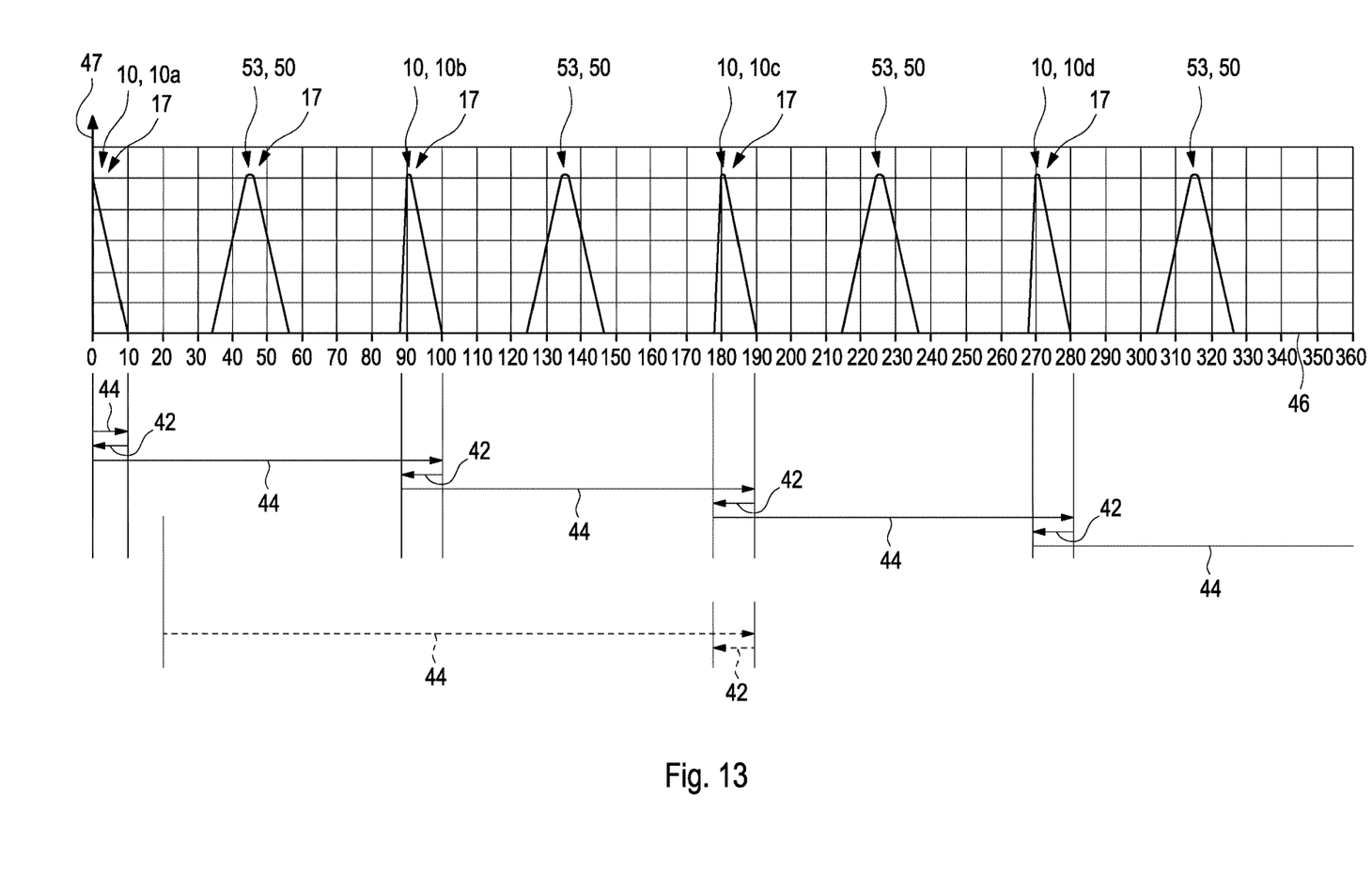
FIG. 13 shows a diagram to explain the mode of operation of the fragrancing system.

Thus for displacing the respective flap 10, one can proceed in accordance with the diagram shown in FIG. 13. Here, in the shown diagram, a rotation angle of the disc 28 and thus of the cam plate structure 29 about the rotation axis 30 is shown along the x-axis 46, and the opening angle of the respective flap 10 is shown along the y-axis 47. Beneath the diagram, the direction 42, 44 of the rotation about the rotation axis 30 is indicated by arrows, wherein in the illustration of FIG. 13, arrows directed towards the right indicate the second rotation direction 44, and the arrows directed towards the left indicate the first rotation direction 42 of the disc 28. Therefore, for example, for opening the first flap 10a into the open position 17 the disc 28 is displaced in first rotation direction 42 between the angle degree 10 and 0. For opening the second flap 10b into the open position 17, the disc 28 is rotated in first rotation direction 42 between the rotation angle 100 and 90. For displacing the third flap 10c into the open position 17, the disc 28 is displaced in first rotation direction 42 between the angle degree 190 and 180. For displacing the fourth flap 10d into the open position 17, the disc 28 is displaced in first rotation direction 42 between the angle degree 280 and 270. The respective flap 10 is displaced here only into the associated angle range and on rotation about the rotation axis 30 in first direction 42 into the open position 17 and is situated otherwise in the closed position 16. For displacing the respective flap 10 from the open position 17 into the closed position 16, the disc 28 is therefore rotated in second rotation direction 44. In the illustration of the arrows symbolising the rotation directions 42, 44 in FIG. 13, it is assumed here that the flaps 10 are opened and closed in succession. It is therefore assumed that firstly the first flap 10a is opened and subsequently closed, thereafter the second flap 10b is opened and subsequently closed, thereafter the third clap 10c is opened and subsequently closed and thereafter the fourth flap 10d is opened and subsequently closed. Of course, it is also conceivable to open or to close the flaps 10 respectively as desired. If an opening of one of the flaps 10 is desired, the disc 28 is rotated in second rotation direction 44 until the angle range is reached in which the flap 10 which is to be opened is opened. On reaching this angle range, the disc 28 is rotated in the corresponding angle range in first rotation direction 42. When, therefore, for example the rotary disc 28 is situated at a rotation angle of 20 degrees and the third flap 10c is to be opened next, the disc 28, as indicated by dashed arrows, is then firstly displaced in second rotation direction 44 to the angle position of 190 degrees and subsequently into first direction 42 into the angle position of 180 degrees.

Figure 14:
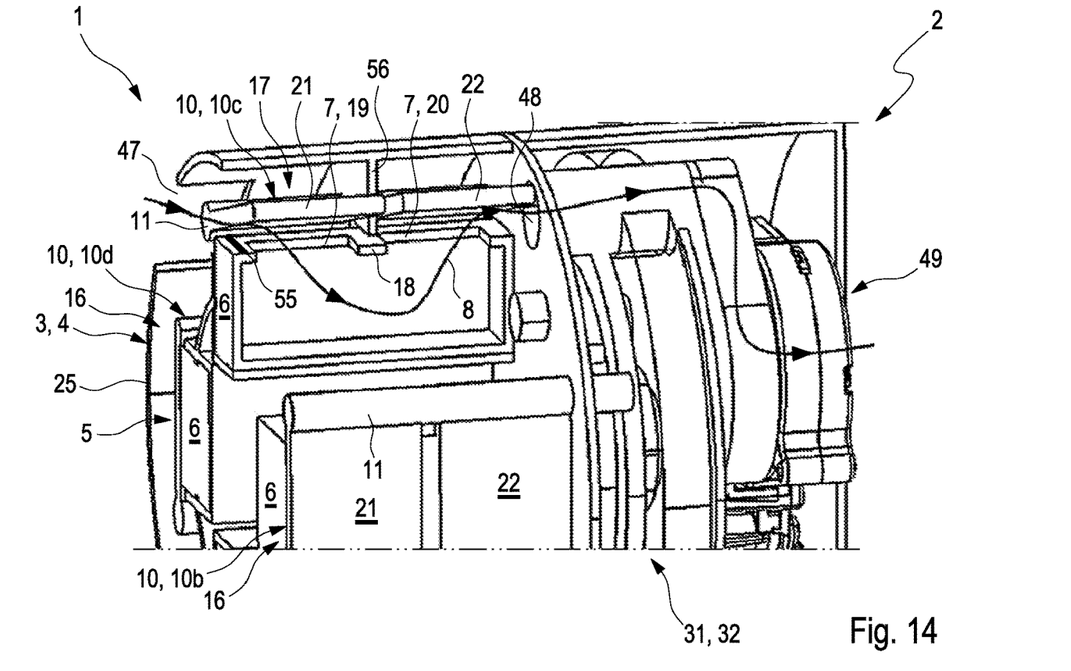
FIG. 14 shows an isometric, cut view of the fragrancing system.

As can be seen in particular from FIG. 14, the flow path 8 leads through at least one inlet opening 47 of the ventilation system 1 into the chamber 5 and through at least one outer opening 48 of the ventilation system 1 out of the chamber 5. In the shown example embodiment, four such inlet openings 47 are provided, which are formed respectively radially on the outer side and axially on the face side of the casing portion 25 (see FIG. 1). The inlet openings 47 and the outer openings 48 are respectively spaced apart with respect to the cartridge openings 7. As the direction of the flow path 8 in FIG. 14 shows, here the air is preferably drawn out of the chamber 5 through the at least one outer opening 48. For this purpose, the fragrancing system 1, as shown in FIG. 14, can have a conveying device 49 which, in operation, draws air through the at least one outer opening 48 and out of the chamber 5.

The at least one inlet opening 47 and the at least one outer opening 48 are spaced apart with respect to one another axially in such a way that the flow path 8 in the open position 17 of the respective flap 10 flows through the first opening portion 19 of the associated cartridge opening 7 into the cartridge 6 and through the second opening portion 20 out of the cartridge opening 7.

Figure 15:
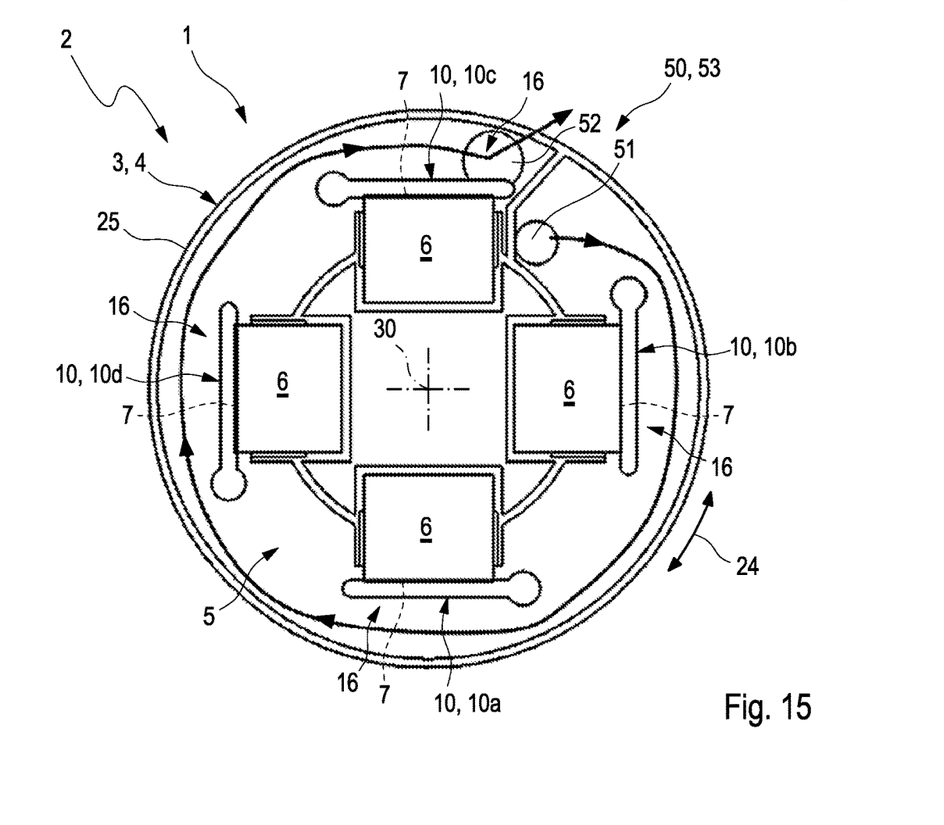
FIG. 15 shows a section through the fragrancing system in another example embodiment.

In FIG. 15 another example embodiment of the fragrancing system 1 is shown, which differs from the previously shown example embodiments in that the fragrancing system 1 has a valve device 50 which, in particular driven by the actuating mechanism 27, respectively is then opened when the flaps 10 of the closing mechanisms 9 are respectively displaced in the closed position 16, in order to flush the chamber 5 and thus to free it of fragrance which is possibly present in the chamber 5. For this purpose, the valve device 50 has between the at least one inlet opening 47 and the at least one outer opening 48 a valve inlet 51 and a valve outlet 52, which in a release state 53 of the valve device 50 shown in FIG. 15 are respectively fluidically connected with the chamber 5, so that the chamber 5, as indicated by arrows in FIG. 15, is flushed. The fragrancing system 1, as shown in FIG. 13, is preferably configured here such that between successive open positions 17 of the flaps 10 respectively a release state 53 of the valve device 50 takes place, in order to flush the chamber 5.

Figure 6:
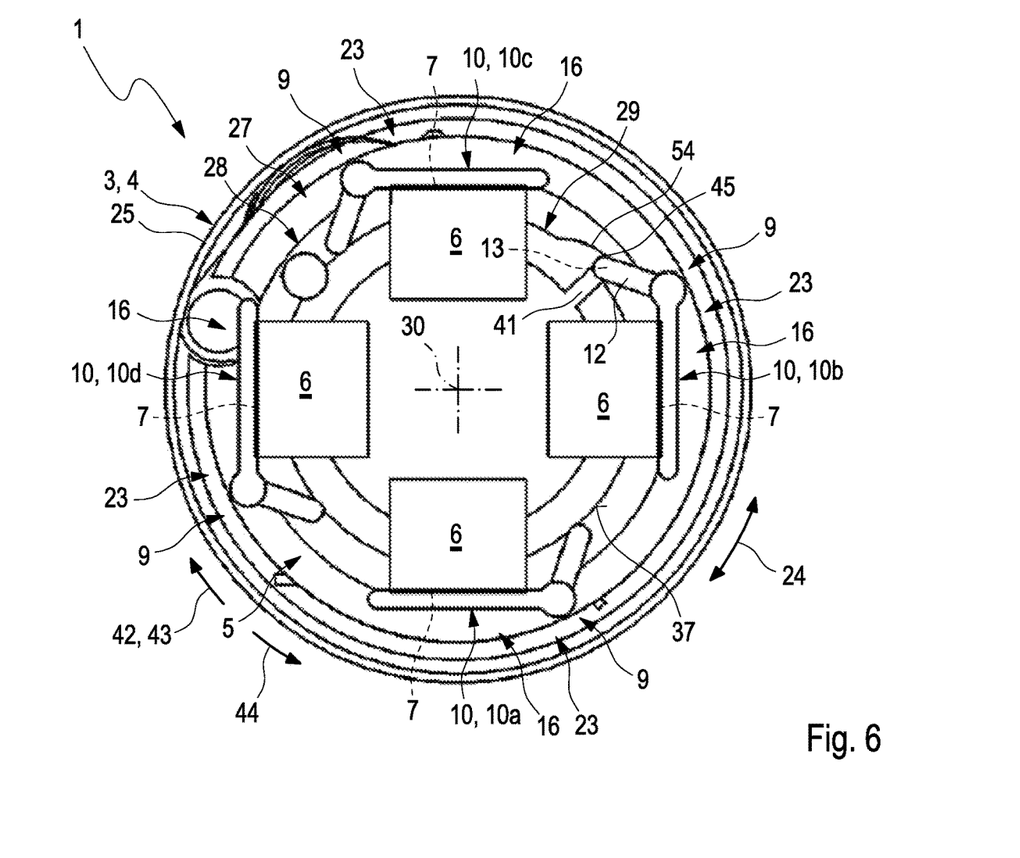
FIG. 6 shows a section through the fragrancing system.

As can be seen in particular from FIG. 6, the sliding of the respective pin 13 over the recess 41 on rotation of the disc 28 about the rotation axis 30 in second rotation direction 44 can be improved in that on the outer side 37 of the cam plate structure 29 on the side in circumferential direction 24 along the second rotation direction 44 following the outer opening 45 or respectively the first rotation direction 42 preceding the outer opening 45, a radial elevation 54 is formed. In addition, the displacing of the respective pin 13 into the recess 41 is thus improved in that on rotation of the disc 28 in first rotation direction 42, the pin 13 strikes in circumferential direction 24 against the elevation 54 and is subsequently acted upon into the recess 41.

Preferably, the respective cartridge opening 7 is surrounded by a seal 55, which is indicated only in FIG. 14 and there only partially, on which seal the associated flap 10 rests in the closed position 16. The respective seal 55 is softer here than the associated flap 10.

As can be seen further in particular from FIG. 14, the fragrancing system 1, in particular the casing 3, has a rib 56 penetrating radially into the chamber and running in an annular manner in circumferential direction 24. The rib 56 is aligned radially with the respective web 18, lies in particular radially on the outer side on the respective web 18. The chamber 5 is thus divided radially on the outer side into a first portion associated with the respective first opening portion 19 and first flap portion 21 and a second portion associated with the respective second opening portion 20 and the second flap portion 22.

Figure 3:
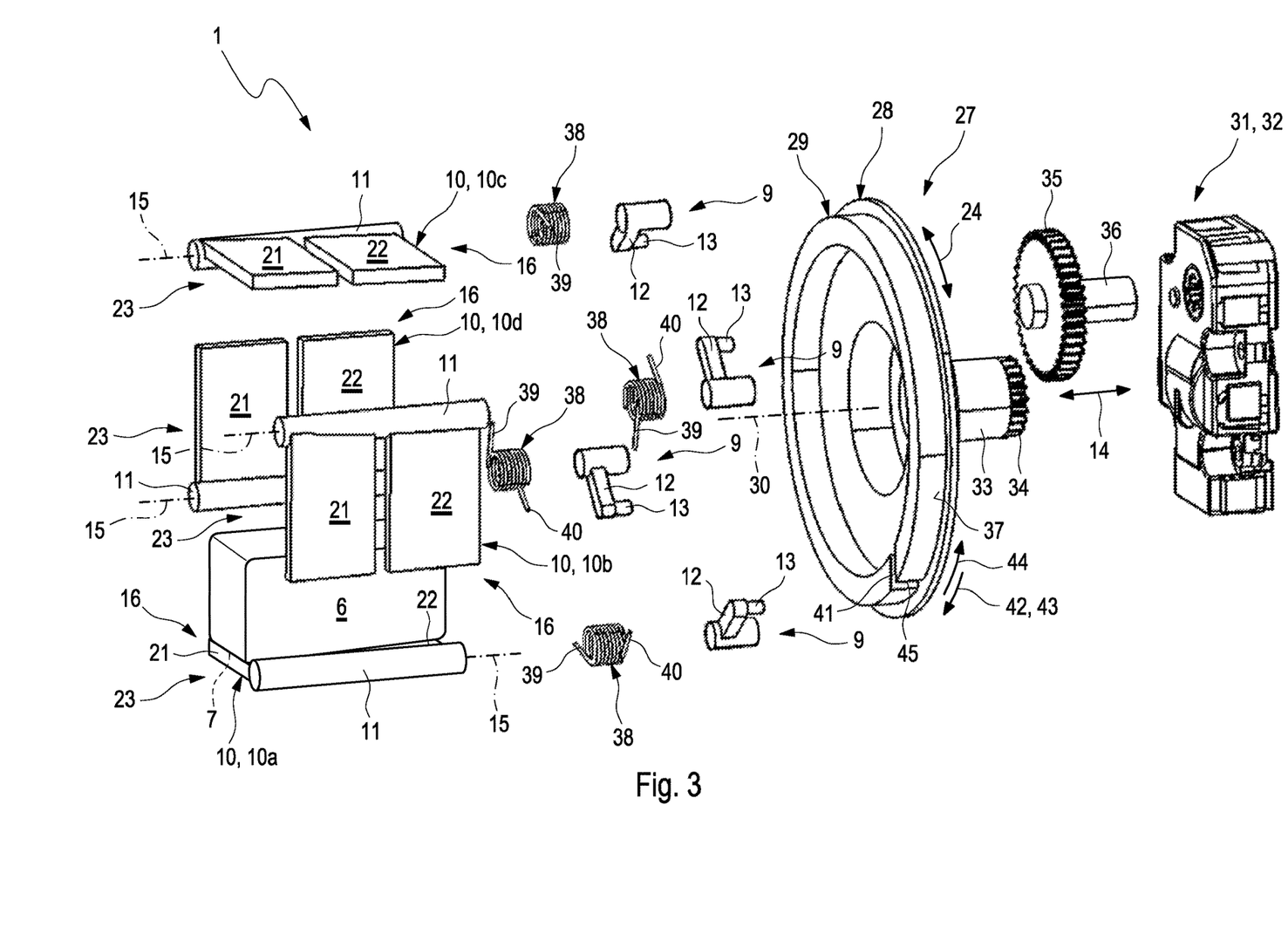
FIG. 3 shows an isometric exploded illustration of the fragrancing system.
Figure 4:
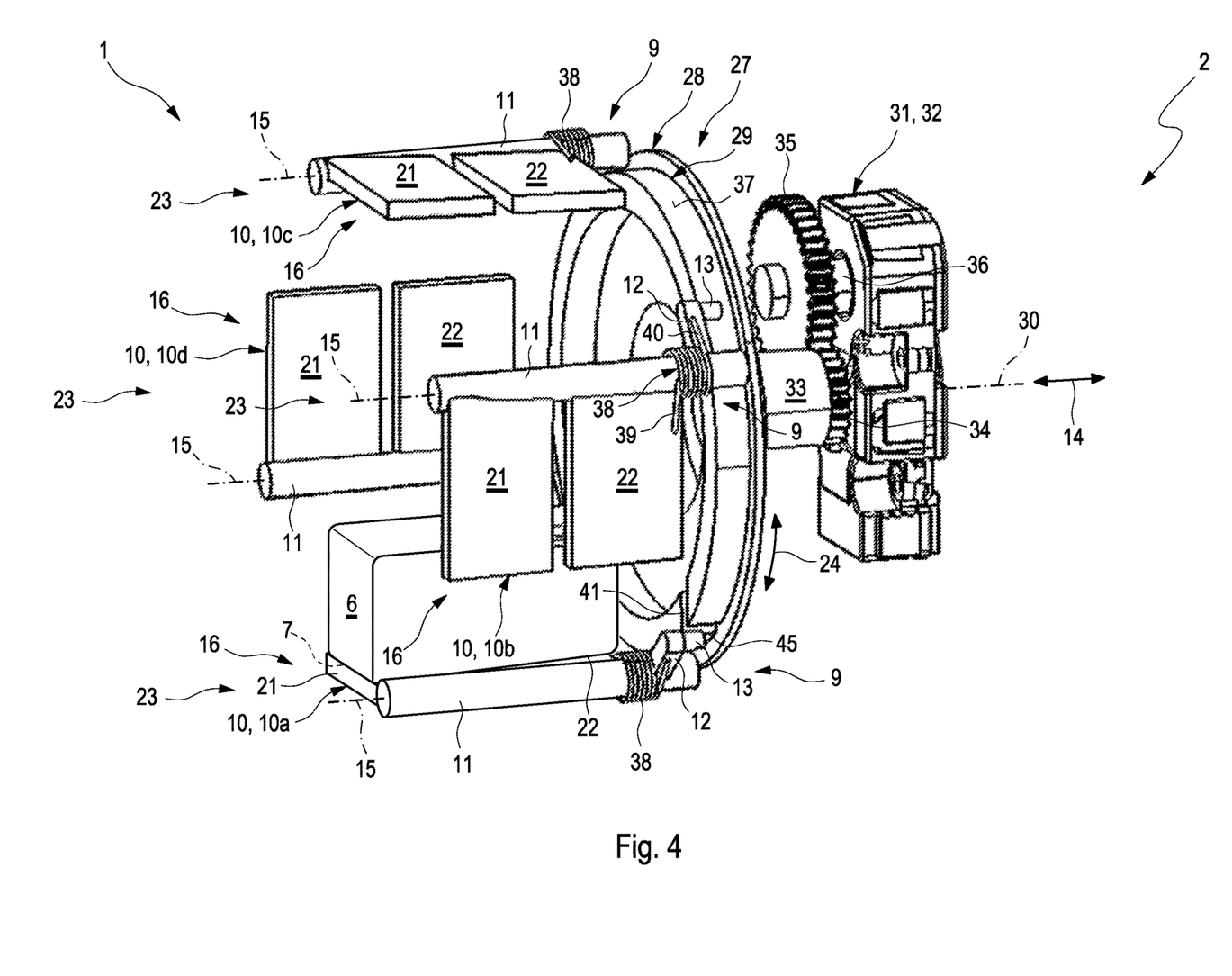
FIG. 4 shows an isometric interior view of the fragrancing system.
Figure 5:
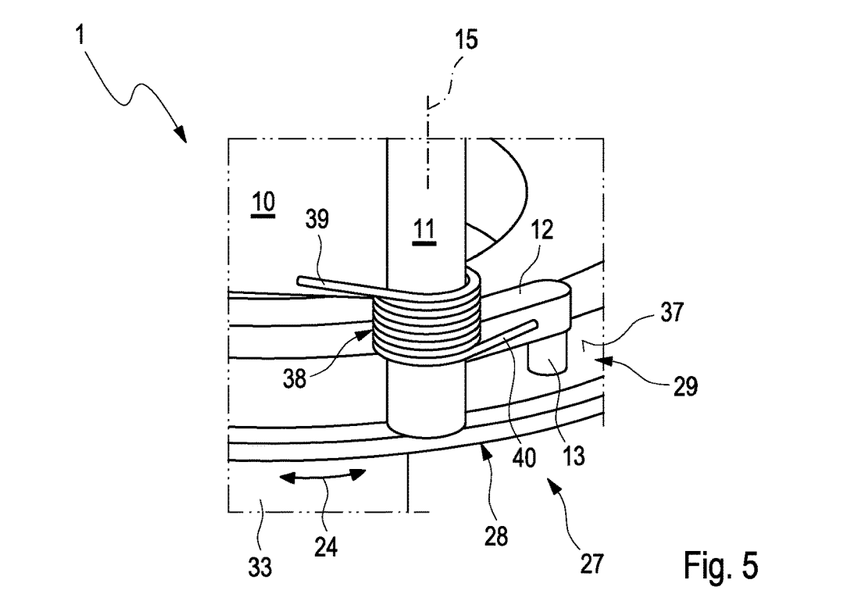
FIG. 5 shows an isometric view of a detail of the fragrancing system.

As can be seen for example from FIG. 3, in the shown example embodiments the respective lever 12 and the associated pin 13 of the respective closing mechanism 9 are produced jointly and in one piece. In addition, the respective shaft 11 and the associated flap 10 of the respective closing mechanism 9 are produced jointly and in one piece.

The invention claimed is:

1. A fragrancing system comprising:
at least one cartridge for storing a fragrance, the at least one cartridge having a cartridge opening;
at least one closing mechanism including a flap and a shaft extending along an axial direction non-rotatably connected to the shaft, via a rotation of the shaft about a pivot axis displaceable to a closed position, in which the flap closes the cartridge opening of an associated cartridge of the at least one cartridge, and an open position, in which the flap frees the cartridge opening of the associated cartridge;
the at least one closing mechanism further including a lever extending transversely to the shaft and mechanically connected with the shaft, and a pin extending axially and connected with the lever;
an actuating mechanism including a disc rotatable about a rotation axis, which extends in an axial direction;
a cam plate structure extending in a circumferential direction, and projecting axially from the disc;
the pin arranged on an outer side of the cam plate structure, which faces radially away from the rotation axis, when the flap is in the closed position;
wherein the at least one closing mechanism is configured to act upon the flap elastically in a direction of the closed position and to act upon the pin elastically in a direction of the outer side of the cam plate structure;
wherein the cam plate structure includes at least one recess disposed in the radial outer side, the at least one recess structured and arranged to engage the pin when the flap is in the open position; and
wherein an actuator is configured to, when in operation, rotate the disc about the rotation axis.

2. The fragrancing system according to claim 1, wherein:
the at least one closing mechanism includes at least two closing mechanisms; and
the at least one recess is structured as a shared recess configured to engage the pin of each of the at least two closing mechanisms.

3. The fragrancing system according to claim 1, wherein the cam plate structure is configured such that the pin, when the disc is rotated about the rotation axis in a first direction, is acted upon into the at least one recess, and, when the disc is rotated about the rotation axis in a second direction opposed to the first direction, slides over the at least one recess.

4. The fragrancing system according to claim 3, wherein the at least one recess has a curvature following the second direction.

5. The fragrancing system according to claim 1, wherein:
the at least one closing mechanism includes at least two closing mechanisms; and the at least one cartridge includes at least two cartridges that are each associated with one of the at least two closing mechanisms and that are disposed spaced apart from one another in the circumferential direction.

6. The fragrancing system according to claim 1, wherein the at least one cartridge is arranged exchangeably.

7. The fragrancing system according to claim 1, wherein the at least one cartridge includes at least two cartridges that are structured identically.

8. The fragrancing system according to claim 1, wherein the lever and the pin are integrally provided as a single piece.

9. The fragrancing system according to claim 1, wherein:
the at least one closing mechanism further includes a rotary spring wound around the pivot axis of the shaft;
the rotary spring includes a first leg acting upon the flap elastically in the direction of the closed position; and
the rotary spring further includes a second leg acting upon the pin in the direction of the outer side of the cam plate structure.

10. The fragrancing system according to claim 1, wherein the at least one closing mechanism includes at least two closing mechanisms that are structured identically.

11. The fragrancing system according to claim 1, further comprising:
a chamber in which the at least one cartridge is arranged; and
a flow path extending through the chamber, through an inlet opening that is disposed spaced apart from the at least one cartridge, and through an outlet opening that is disposed spaced apart from the at least one cartridge.

12. The fragrancing system according to claim 1, further comprising a cylindrical casing surrounding the at least one cartridge and the at least one closing mechanism in the circumferential direction.

13. The fragrancing system according to claim 1, further comprising an output shaft projecting coaxially to the rotation axis from a side of the disc facing axially away from the cam plate structure, wherein the output shaft cooperates with the actuator for rotating the disc about the rotation axis.

14. The fragrancing system according to claim 1, wherein:
the at least one cartridges includes a seal surrounding the cartridge opening;
the seal is softer than the flap; and
the flap is disposed on the seal in a sealing manner when in the closed position.

15. A module for a fragrancing system comprising a cartridge configured to store a fragrance and a closing mechanism, the closing mechanism including:
a shaft extending in an axial direction and pivotable about a pivot axis;
a flap non-rotatably connected to the shaft;
a lever extending transversely to the shaft and mechanically connected to the shaft;
a pin extending axially and connected with the lever;
wherein, via rotation of the shaft about the pivot axis, the flap is adjustable to a closed position, in which the flap closes q cartridge opening, and to an open position, in which the flap does not close the cartridge opening;
wherein the closing mechanism is configured to act upon the flap elastically toward the closed position; and
wherein the closing mechanism is configured to act upon the pin elastically such that, when the flap is in the closed position, the pin is arranged on a radially outward facing outer surface of a cam plate structure of said fragrancing system and, when the flap is in the open position, the pin is engaged with a recess of said cam plate structure.

16. The module according to claim 15, wherein:
the closing mechanism further includes a rotary spring wound around the pivot axis of the shaft;
the rotary spring includes a first leg acting upon the flap elastically in the direction of the closed position; and
the rotary spring further includes a second leg acting upon the pin.

17. The module according to claim 15, wherein:
the cartridge includes a seal extending around the cartridge opening; and
when in the closed position, the flap is disposed on the seal in a sealing manner.

18. The fragrancing system according to claim 2, wherein the at least one cartridge includes at least two cartridges that are each associated with one of the at least two closing mechanisms and that are disposed spaced apart from one another in the circumferential direction.

19. The fragrancing system according to claim 11, further comprising a cylindrical casing surrounding the at least one cartridge and the at least one closing mechanism in the circumferential direction.

20. The fragrancing system according to claim 19, further comprising an output shaft projecting coaxially to the rotation axis from a side of the disc facing axially away from the cam plate structure, wherein the output shaft cooperates with the actuator for rotating the disc about the rotation axis.

* * * * *

UNITED STATES PATENT AND TRADEMARK OFFICE
CERTIFICATE OF CORRECTION

| | | |
|---|---|---|
| PATENT NO. | : 11,865,231 B2 | Page 1 of 1 |
| APPLICATION NO. | : 17/165917 | |
| DATED | : January 9, 2024 | |
| INVENTOR(S) | : Daniel Eberle et al. | |

It is certified that error appears in the above-identified patent and that said Letters Patent is hereby corrected as shown below:

In the Claims

At Column 14, Claim number 15, Line number 9, please change the letter [[q]] to a.

Signed and Sealed this
Twenty-seventh Day of February, 2024

*Katherine Kelly Vidal*

Katherine Kelly Vidal
*Director of the United States Patent and Trademark Office*